US009480452B2

(12) United States Patent
Oikawa

(10) Patent No.: US 9,480,452 B2
(45) Date of Patent: Nov. 1, 2016

(54) RADIOGRAPHIC APPARATUS INCLUDING A BENDING CONSTANT CALCULATING DEVICE AND A TWISTING CONSTANT CALCULATION DEVICE

(75) Inventor: Shiro Oikawa, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 72 days.

(21) Appl. No.: 14/384,265

(22) PCT Filed: Mar. 21, 2012

(86) PCT No.: PCT/JP2012/001953
§ 371 (c)(1),
(2), (4) Date: Sep. 10, 2014

(87) PCT Pub. No.: WO2013/140445
PCT Pub. Date: Sep. 26, 2013

(65) Prior Publication Data
US 2015/0030128 A1    Jan. 29, 2015

(51) Int. Cl.
*A61B 6/00*    (2006.01)
*G21K 1/00*    (2006.01)

(52) U.S. Cl.
CPC ........... *A61B 6/5282* (2013.01); *A61B 6/4233* (2013.01); *A61B 6/4291* (2013.01); *A61B 6/4441* (2013.01); *A61B 6/5211* (2013.01); *A61B 6/5252* (2013.01); *A61B 6/5258* (2013.01)

(58) Field of Classification Search
CPC   A61B 6/4233; A61B 6/4291; A61B 6/5211; A61B 6/5258; A61B 6/5282
USPC .................. 378/62, 154, 155, 207, 19, 98.8; 382/132; 250/370.09
See application file for complete search history.

(56) References Cited

U.S. PATENT DOCUMENTS 8,233,659 B2 * 7/2012 Fujita .................. A61B 6/4441
378/62
8,284,902 B2 * 10/2012 Fujita .................. A61B 6/4233
378/155

(Continued)

FOREIGN PATENT DOCUMENTS

JP    2011-136102 A    7/2011
JP    2011-167334 A    9/2011

(Continued)

OTHER PUBLICATIONS

International Search Report and Written Opinion issued in International Application No. PCT/JP2012/001953 dated Apr. 24, 2012, with partial English translation.

*Primary Examiner* — Allen C. Ho
(74) *Attorney, Agent, or Firm* — McDermott Will & Emery LLP

(57) ABSTRACT

A first and a second accumulated value calculating units are provided which, in a location where foil shadows by grid foil strips straddle pixels, identify this location based on geometry, and calculate straddle accumulated values of the foil shadows in the identified location. Even when the foil shadows by the grid foil strips straddle the pixels due to twisting and bending of the grid foil strips, such location is identified based on geometry and the straddle accumulated values of the foil shadows in the identified location are calculated. Therefore, even when changes are made in the pitches or pixel sizes of an X-ray grid and a flat panel X-ray detector (FPD), the foil shadows will be removed based on the straddle accumulated values. As a result, the foil shadows can be removed taking twisting and bending of the grid foil strips into consideration, and in a way to accommodate X-ray grids and FPDs of various sizes.

5 Claims, 8 Drawing Sheets

(56) References Cited

U.S. PATENT DOCUMENTS

| | | | | |
|---|---|---|---|---|
| 8,406,376 B2* | 3/2013 | Hirooka | | A61B 6/00 378/98.4 |
| 8,494,118 B2* | 7/2013 | Oikawa | | A61B 6/4291 378/207 |
| 8,559,754 B2* | 10/2013 | Fujita | | A61B 6/4291 128/922 |
| 8,712,715 B2* | 4/2014 | Tonami | | A61B 6/5258 378/163 |
| 8,737,568 B2* | 5/2014 | Fujita | | A61B 6/4233 378/154 |
| 2011/0158388 A1 | 6/2011 | Hirooka | | |
| 2011/0200169 A1 | 8/2011 | Oikawa | | |
| 2011/0238354 A1 | 9/2011 | Tonami | | |
| 2012/0063699 A1 | 3/2012 | Fujita | | |

FOREIGN PATENT DOCUMENTS

| | | |
|---|---|---|
| WO | 2010/064287 A1 | 6/2010 |
| WO | 2010/134295 A1 | 11/2010 |

\* cited by examiner

RADIOGRAPHIC APPARATUS INCLUDING A BENDING CONSTANT CALCULATING DEVICE AND A TWISTING CONSTANT CALCULATION DEVICE

CROSS REFERENCE TO RELATED APPLICATIONS

This application is a U.S. National Stage application under 35 U.S.C. §371, of International Application PCT/JP2012/001953 filed on Mar. 21, 2012, which was published as WO 2013/140445 on Sep. 26, 2013, the disclosure of which is incorporated herein by reference.

TECHNICAL FIELD

This invention relates to a radiographic apparatus for obtaining radiological images, and more particularly to a technique for removing scattered radiation using a radiation grid.

BACKGROUND ART

A conventional radiographic apparatus has a radiation grid for removing scattered radiation in order to prevent scattered radiation from an inspection object from impinging on a flat panel radiation detector (radiation detecting device). The radiation grid is formed of an alternate arrangement of grid foil strips which absorb the scattered radiation and interspacers which transmit the radiation. The grid foil strips are formed of a material such as lead which absorbs radiation, typically X-rays. The interspacers are formed of an intermediate material such as aluminum or an organic material which transmits radiation, typically X-rays. However, when the radiation passes through the interspacers, the radiation (direct radiation) other than the scattered radiation will also be absorbed by the intermediate material. So an air grid, in which the interspacers are made voids for reliably transmitting the radiation (direct radiation) other than the scattered radiation, has been used as radiation grid in recent years.

Incidentally, in portions where the direct radiation is blocked by the grid foil strips, foil shadows due to the grid foil strips appear in radiological images. So, Applicant herein has proposed false image removing methods for removing false images resulting from the foil shadows (see Patent Documents 1 and 2, for example).

PRIOR ART DOCUMENTS

Patent Documents

[Patent Document 1]
International Publication WO2010-064287
[Patent Document 2]
Japanese Unexamined Patent Publication No. 2011-167334

SUMMARY OF INVENTION

Technical Problem

However, the air grid, since the interspacers noted above are voids, easily produces false images due to twisting and bending of the grid foil strips. A false image removing process has been conducted until now with the air grid having grid foil strips arranged synchronously with respective pixels (eg synchronously with every four pixels) forming a radiological image obtained with a flat panel radiation detector (FPD: Flat Panel Detector). It is desired that an appropriate false image removing process is made possible also for the case of grid foil strips in a focusing distance arrangement which is asynchronous. In other words, it is unrealistic to manufacture air grids of sizes compatible and individually synchronized with various FPD pixel sizes.

This invention has been made having regard to the state of the art, and its object is to provide a radiographic apparatus which can remove foil shadows in a way to accommodate radiation grids and radiation detecting devices of various pitches or pixel sizes, while taking into consideration twisting and bending of grid foil strips.

Solution to Problem

To fulfill the above object, this invention provides the following construction.

A radiographic apparatus according to this invention (radiographic apparatus according to the former invention) is a radiographic apparatus for obtaining a radiological image, comprising a radiation source for emitting radiation; a radiation detecting device for detecting the radiation emitted; and a radiation grid disposed adjacent a detecting plane of the radiation detecting device, and having an arrangement of grid foil strips for absorbing scattered radiation; the radiographic apparatus further comprising an accumulated value calculating device which, in a location where foil shadows by the grid foil strips straddle pixels, identifies the location based on a mutual geometric positional relationship of the radiation source, the radiation detecting device and the radiation grid, and calculates a straddle accumulated value of the foil shadows in the identified location; a radiological image collecting device for collecting an actual radiological image based on radiation detection signals detected in the presence of an inspection object; and a bending constant calculating device for calculating a bending constant which is a constant relating to bending of the grid foil strips in the location where the foil shadows by the grid foil strips straddle the pixels; wherein the radiological image is finally obtained by removing the foil shadows by the grid foil strips based on the accumulated value calculating device, the bending constant calculating device and the radiological image collecting device.

A radiographic apparatus according to the latter invention, which is different from the radiographic apparatus according to the former invention, is a radiographic apparatus for obtaining a radiological image, comprising a radiation source for emitting radiation; a radiation detecting device for detecting the radiation emitted; and a radiation grid disposed adjacent a detecting plane of the radiation detecting device, and having an arrangement of grid foil strips for absorbing scattered radiation; the radiographic apparatus further comprising an accumulated value calculating device which, in a location where foil shadows by the grid foil strips straddle pixels, identifies the location based on a mutual geometric positional relationship of the radiation source, the radiation detecting device and the radiation grid, and calculates a straddle accumulated value of the foil shadows in the identified location; a radiological image collecting device for collecting an actual radiological image based on radiation detection signals detected in the presence of an inspection object; and a twisting constant calculating device for calculating a bending constant which is a constant relating to bending of the grid foil strips in the location where the foil shadows by the grid foil strips straddle the pixels; wherein the radiological image is finally obtained by removing the foil shadows by the grid foil strips based on the accumulated value calculating device, the twisting constant calculating device and the radiological image collecting device.

The radiographic apparatus according to the former and latter inventions include, besides the radiation source, radiation detecting device and radiation grid, an accumulated value calculating device which, in a location where the foil shadows by the grid foil strips straddle pixels, identifies this location based on a mutual geometric positional relationship of the radiation source, radiation detecting device and radiation grid, and calculates a straddle accumulated value of the foil shadows in the identified location. And the radiological image collecting device is provided for collecting an actual radiological image based on radiation detection signals detected in the presence of an inspection object. A radiological image is finally obtained by removing the foil shadows by the grid foil strips based on the above accumulated value calculating device and the above radiological image collecting device. Even when the foil shadows by the grid foil strips straddle the pixels due to twisting and bending of the grid foil strips, such location is identified based on the mutual geometric positional relationship (that is, geometry) of the radiation source, radiation detecting device and radiation grid, and the straddle accumulated value of the foil shadows in the identified location is calculated. Therefore, even when changes are made in the sizes of the radiation grid and radiation detecting device, the foil shadows will be removed based on the straddle accumulated value. As a result, the foil shadows can be removed taking twisting and bending of the grid foil strips into consideration, and in a way to accommodate radiation grids and radiation detecting devices of various sizes. Twisting or bending of each grid foil strip does not necessarily cause its foil shadow to straddle or cover the pixels. Note that pixels in a location considered likely to be straddled by the foil shadow are recognized from geometry, and a straddle accumulated value in that location is calculated uniformly, regardless of a foil shadow straddle situation.

The radiographic apparatus according to the former invention comprises a bending constant calculating device for calculating a bending constant which is a constant relating to bending of the grid foil strips in the location where the foil shadows by the grid foil strips straddle the pixels; wherein the radiological image is finally obtained by removing the foil shadows by the grid foil strips based on the accumulated value calculating device, the bending constant calculating device and the radiological image collecting device. By removing the foil shadows by the grid foil strips using also the bending constant which is a numerical expression of bending, the foil shadows can be removed with increased precision through greater consideration made of the bending of the grid foil strips.

The radiographic apparatus according to the latter invention comprises a twisting constant calculating device for calculating a twisting constant which is a constant relating to twisting of the grid foil strips; wherein the radiological image is finally obtained by removing the foil shadows by the grid foil strips based on the accumulated value calculating device, the twisting constant calculating device and the radiological image collecting device. By removing the foil shadows by the grid foil strips using also the twisting constant which is a numerical expression of twisting, the foil shadows can be removed with increased precision through greater consideration made of the twisting of the grid foil strips. The radiographic apparatus according to the former invention (radiographic apparatus with the bending constant calculating device) and the radiographic apparatus according to the latter invention (radiographic apparatus with the twisting constant calculating device) may be combined. That is, the radiological image may be finally obtained by removing the foil shadows by the grid foil strips based on the accumulated value calculating device, the bending constant calculating device, the twisting constant calculating device and the radiological image collecting device.

It is preferred that these radiographic apparatus according to this invention comprises an accumulated value multiplying device for multiplying the straddle accumulated value of reference correction data based on X-ray detection signals detected in the absence of the inspection object by a predetermined multiplying factor based on width and pixel size of the foil shadows. By multiplying the straddle accumulated value of the reference correction data by the predetermined multiplying factor, the radiological image without the foil shadows can be obtained in a way to accommodate the radiation grids and radiation detecting devices of various sizes. It is therefore possible to perform an appropriate false image removing process using one radiation grid, without manufacturing a radiation grid according to each radiation detecting device or geometry.

Advantageous Effects of Invention

The radiographic apparatus according to the former and latter inventions include the accumulated value calculating device which, in a location where the foil shadows by the grid foil strips straddle pixels, identifies this location based on a mutual geometric positional relationship of the radiation source, radiation detecting device and radiation grid, and calculates a straddle accumulated value of the foil shadows in the identified location. Even when the foil shadows by the grid foil strips straddle the pixels due to twisting and bending of the grid foil strips, such location is identified based on geometry and the straddle accumulated value of the foil shadows in the identified location is calculated. Therefore, even when changes are made in the sizes of the radiation grid and radiation detecting device, the foil shadows will be removed based on the straddle accumulated value. As a result, the foil shadows can be removed taking twisting and bending of the grid foil strips into consideration, and in a way to accommodate radiation grids and radiation detecting devices of various sizes.

With the radiographic apparatus according to the former invention, by removing the foil shadows by the grid foil strips using also the bending constant which is a numerical expression of bending, the foil shadows can be removed with increased precision through greater consideration made of the bending of the grid foil strips.

With the radiographic apparatus according to the latter invention, by removing the foil shadows by the grid foil strips using also the twisting constant which is a numerical expression of twisting, the foil shadows can be removed with increased precision through greater consideration made of the twisting of the grid foil strips.

DESCRIPTION OF EMBODIMENTS

Figure 1:
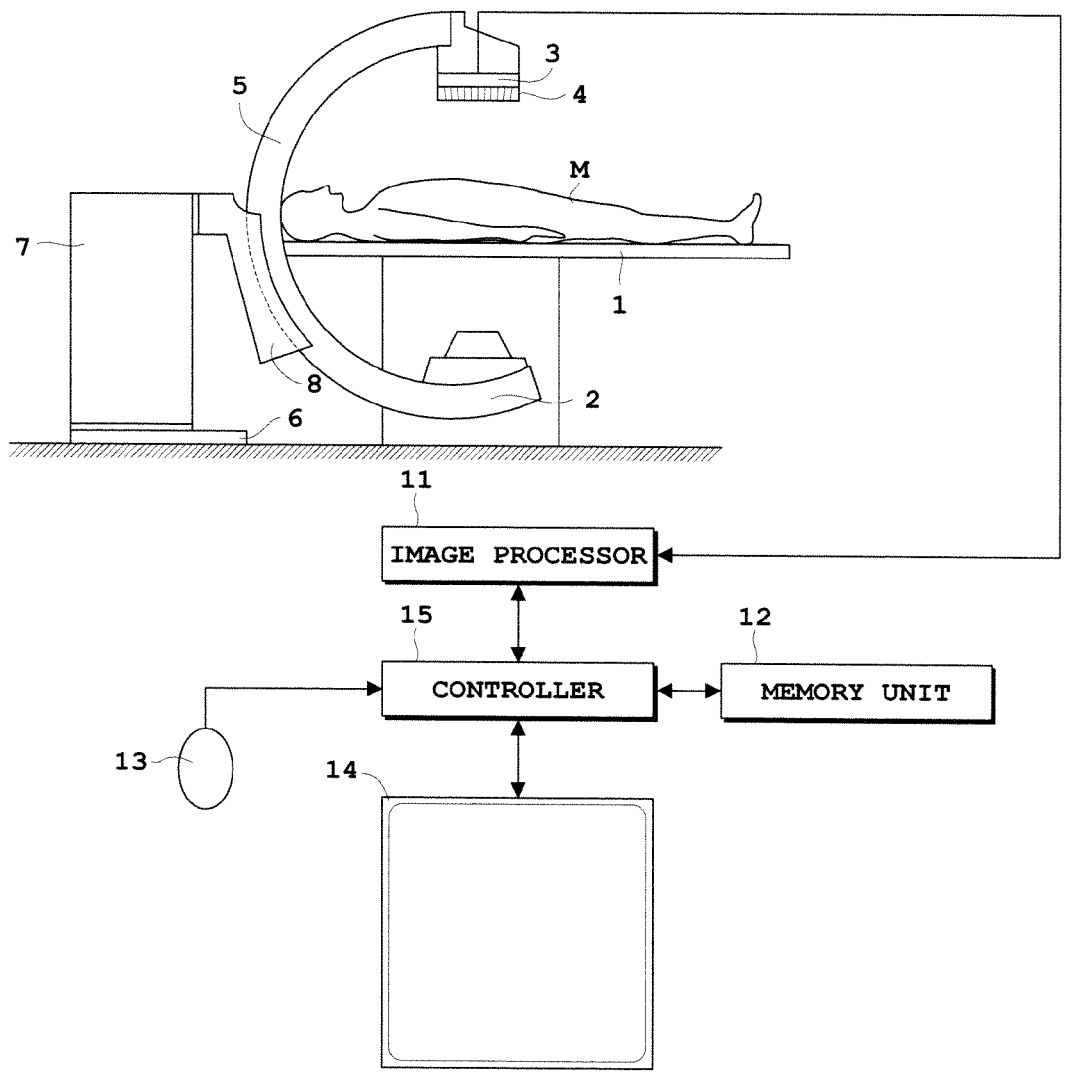
FIG. 1 is an outline view and block diagram of an X-ray apparatus according to an embodiment.
Figure 2:
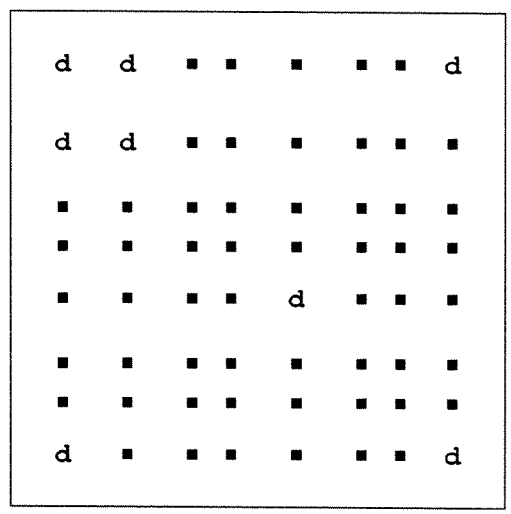
FIG. 2 is a schematic view of a detecting plane of a flat panel X-ray detector (FPD)
Figure 3:
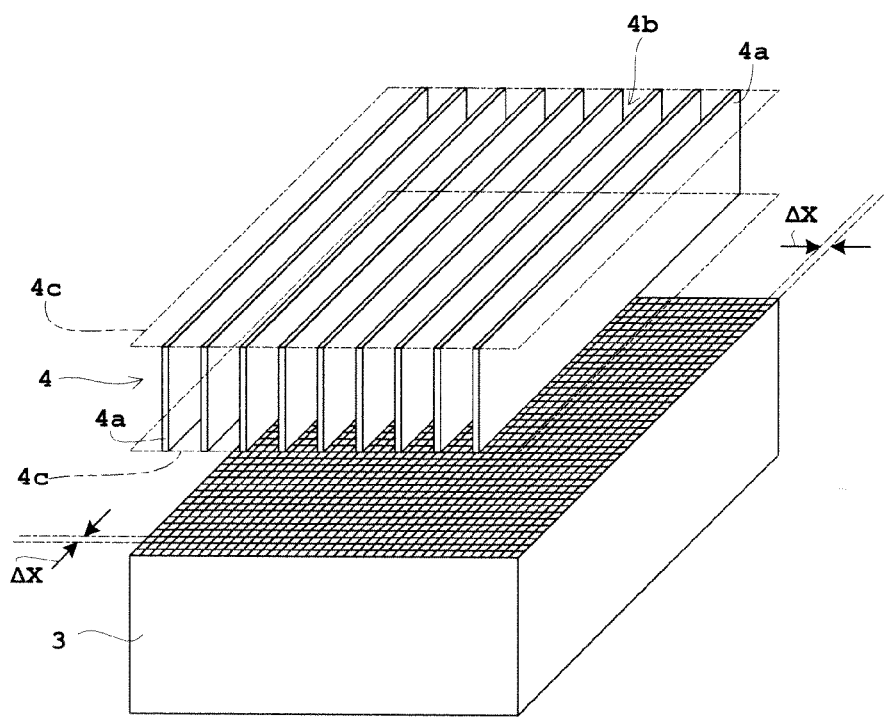
FIG. 3 is a schematic view of an X-ray grid.

An embodiment of this invention will be described hereinafter with reference to the drawings. FIG. 1 is an outline view and block diagram of an X-ray apparatus according to the embodiment. FIG. 2 is a schematic view of a detecting plane of a flat panel X-ray detector (FPD). FIG. 3 is a schematic view of an X-ray grid. This embodiment will be described taking X-rays as an example of radiation. An X-ray apparatus having a C-arm for application to systems used for cardiovascular diagnosis (CVS: cardiovascular systems) will be described as an example of radiographic apparatus. An air grid with interspacers made voids, which is a focused grid with grid foil strips arranged along rays converging on an X-ray tube, will be described as an example of radiation grid.

As shown in FIG. 1, the X-ray apparatus according to this embodiment includes a top board 1 for supporting an inspection object M, an X-ray tube 2 for emitting X-rays, a flat panel X-ray detector (hereinafter abbreviated as "FPD") 3 for detecting the X-rays emitted, and an X-ray grid 4 disposed adjacent a detecting plane of the FPD 3 and having an arrangement of grid foil strips 4a (see FIG. 3, for example) for absorbing scattered X-rays. The X-ray tube 2 corresponds to the radiation source in this invention. The flat panel X-ray detector (FPD) 3 corresponds to the radiation detecting device in this invention. The X-ray grid 4 corresponds to the radiation grid in this invention.

In addition, the X-ray apparatus includes a C-arm 5 which holds the X-ray tube 2 at one end thereof, and holds the FPD 3 along with the X-ray grid 4 at the other end. In FIG. 1, the C-arm 5 is formed in the shape of a curve in the body axis direction of the inspection object M. The C-arm 5 is rotatable along the C-arm 5 itself and about a rotation center axis perpendicular to the body axis of the inspection object M, whereby the X-ray tube 2, FPD 3 and X-ray grid 4 held by the C-arm 5 can also be rotated in the same direction. Further, the C-arm 5 is rotatable about a rotation center axis perpendicular to the body axis, whereby the X-ray tube 2, FPD 3 and X-ray grid 4 can also be rotated in the same direction.

Specifically, the C-arm 5 is held by a base block 6 fixed to a floor, through a strut 7 and an arm holder 8. The strut 7 is rotatable about a vertical axis relative to the base block 6, and with this rotation the X-ray tube 2, FPD 3 and X-ray grid 4 can also be rotated in the same direction together with the C-arm 5 held by the strut 7. With the arm holder 8 held by the strut 7 to be rotatable about the body axis of the inspection object M, the X-ray tube 2, FPD 3 and X-ray grid 4 can also be rotated in the same direction together with the C-arm 5 held by the arm holder 8. With the C-arm 5 held by the arm holder 8 to be rotatable about the rotation center axis, the X-ray tube 2, FPD 3 and X-ray grid 4 can also be rotated in the same direction together with the C-arm 5.

Further, a construction may be provided for moving the FPD 3 to and fro along an emission axis of X-rays linking the X-ray tube 2 and FPD 3, or to and fro in a focus line direction perpendicular to the emission axis. Even under a condition that the positional relationship between the X-ray tube 2, FPD 3 and X-ray grid 4 should be constant, shifting may be caused, for example by rotation of the C-arm 5, in the positional relationship between the X-ray tube 2, FPD 3 and X-ray grid 4 (transverse focal shift amount=Xf to be described hereinafter).

Further, the X-ray apparatus includes an image processor 11 for carrying out various image processes based on X-ray detection signals detected by the FPD 3, a memory unit 12 for writing and storing reference correction data obtained in advance of X-raying and data of each image obtained by the image processor 11, for example, an input unit 13 for inputting data and commands, a display unit 14 for displaying images obtained by the image processor 11, and a controller 15 for performing overall control of these components. In addition, a high voltage generator, for example, is provided for generating high voltage and applying tube current and tube voltage to the X-ray tube 2. However, this does not constitute the characterizing part of this invention or is not a component relating to the characterizing part, and is therefore omitted from the drawings.

The memory unit 12, through the controller 15, writes and stores the reference correction data and data of each image obtained by the image processor 11, which are read as appropriate if necessary, and through the controller 15, these data are fed to and displayed on the display unit 14. The memory unit 12 is formed of a storage medium represented by a ROM (Read-only Memory), a RAM (Random-Access Memory), a hard disk and so on.

The input unit 13 feeds into the controller 15 the data and commands inputted by the operator. The input unit 13 is formed of a pointing device represented by a mouse, a keyboard, a joystick, a trackball, a touch panel and so on. The display unit 14 is formed of a monitor.

The image processor 11 and controller 15 are formed of a central processing unit (CPU) and others. The data of each image obtained by the image processor 11 is written and stored through the controller 15 in the memory unit 12, or is fed into and displayed on the display unit 14. A specific construction of the image processor 11 will be described in detail hereinafter.

The FPD 3, as shown in FIG. 2, has a plurality of detecting elements d sensitive to X-rays and arranged in a two-dimensional matrix form on the detecting plane thereof. The detecting elements d detect X-rays by converting the X-rays transmitted through the inspection object M into X-ray detection signals (electric signals) to be stored once, and reading the X-ray detection signals stored. The X-ray detection signal detected by each detecting element d is converted into a pixel value corresponding to the X-ray detection signal. An X-ray image is outputted by allotting the pixel values to pixels corresponding to positions of the detecting elements d. The X-ray image is fed to the image processor 11.

The X-ray grid 4, as shown in FIG. 3, has an alternate arrangement of grid foil strips 4a for absorbing scattered X-rays and interspacers 4b for transmitting X-rays. The grid foil strips 4a and interspacers 4b are covered by grid covers 4c located on an X-ray incidence plane and on an opposite plane with the grid foil strips 4a and interspacers 4b in between. In order to clarify illustration of the grid foil strips 4a, the grid covers 4c are shown in two-dot chain lines, and other details of the X-ray grid 4 (eg a structure for supporting the grid foil strips 4a) are not shown. The grid foil strips 4a correspond to the grid foil strips in this invention.

As shown in FIG. 3, the X-ray grid 4 is placed to have the respective grid foil strips 4a arranged parallel to the detecting plane of the FPD 3. In this embodiment, the interspacers 4b are voids, and the X-ray grid 4 is also an air grid. The grid foil strips 4a are not limited to a particular material as long as it absorbs radiation represented by X-rays, such as lead. In this embodiment, it is a focused grid having the grid foil strips 4a arranged along rays converging on the X-ray tube 2 (see FIG. 1), but for expediency of illustration, the respective grid foil strips 4a are arranged parallel in FIG. 3.

Assuming that each pixel size is ΔX as shown in FIG. 3, the grid foil strips 4a are arranged synchronously with the respective pixels in this embodiment for facility of understanding. That is, in FIGS. 5 and 7 where distortion (bending and twisting) information on the grid foil strips 4a is collected, the grid foil strips 4a are arranged synchronously with every four pixels. Therefore, with the grid foil strips 4a absorbing X-rays, foil shadows are produced on the FPD 3 and the foil shadows appear on X-ray images, but the grid foil strips 4a are arranged so that the foil shadows may appear synchronously with the respective pixels.

Figure 4:
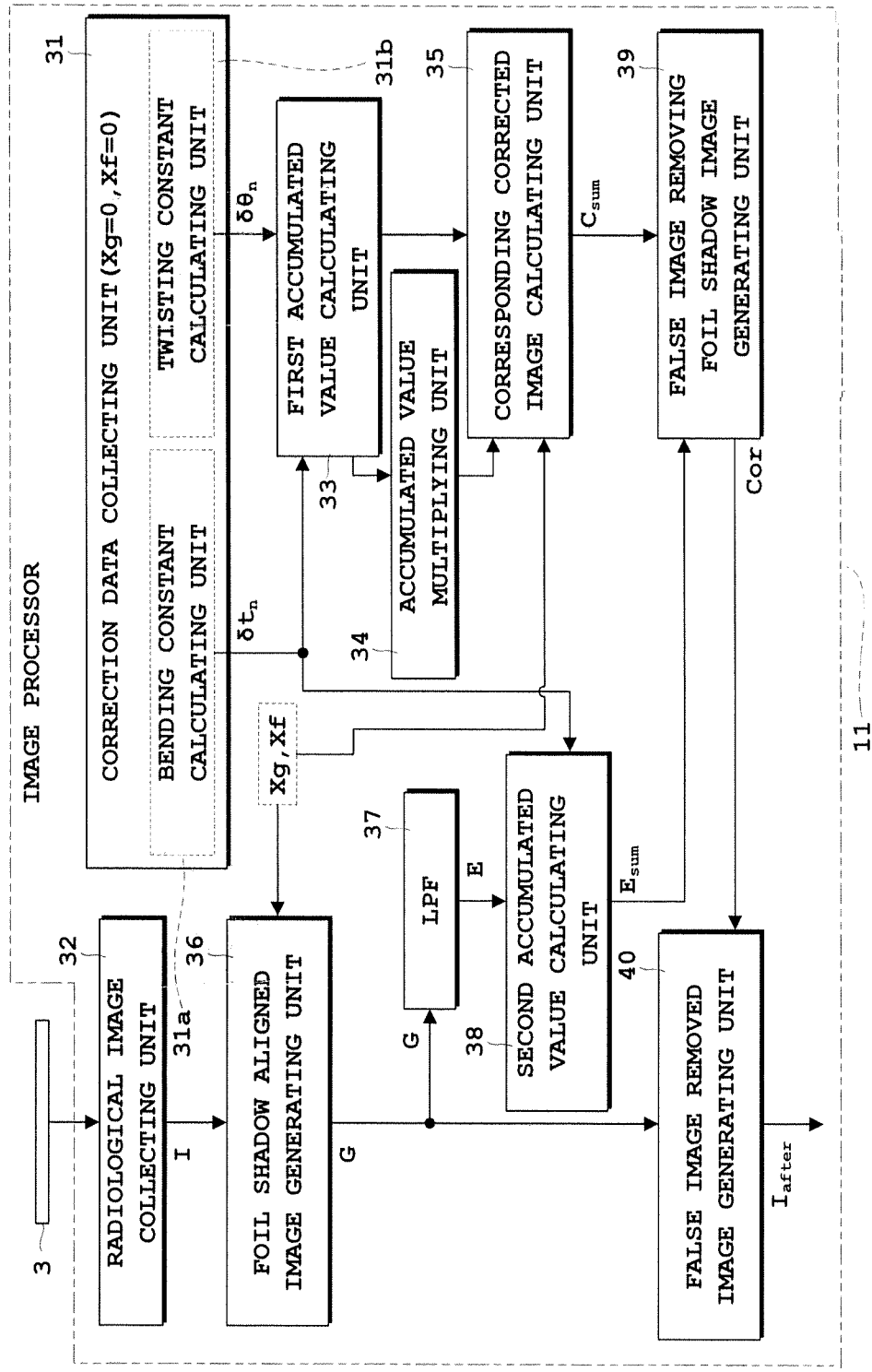
FIG. 4 is a block diagram of a specific image processor according to the embodiment.
Figure 5:
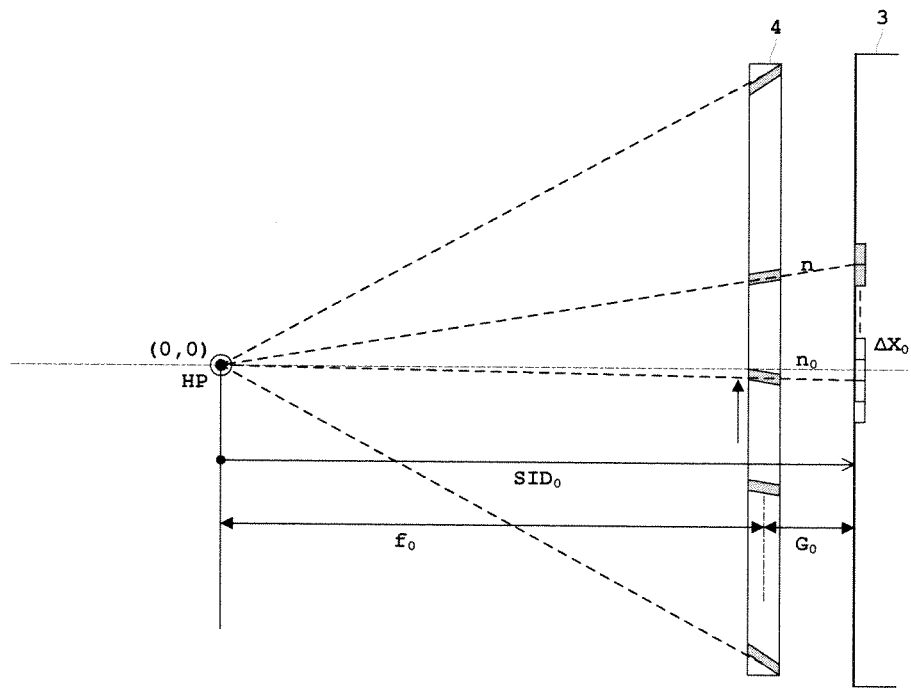
FIG. 5 is a schematic view showing a positional relationship when obtaining a bending constant.
Figure 6:
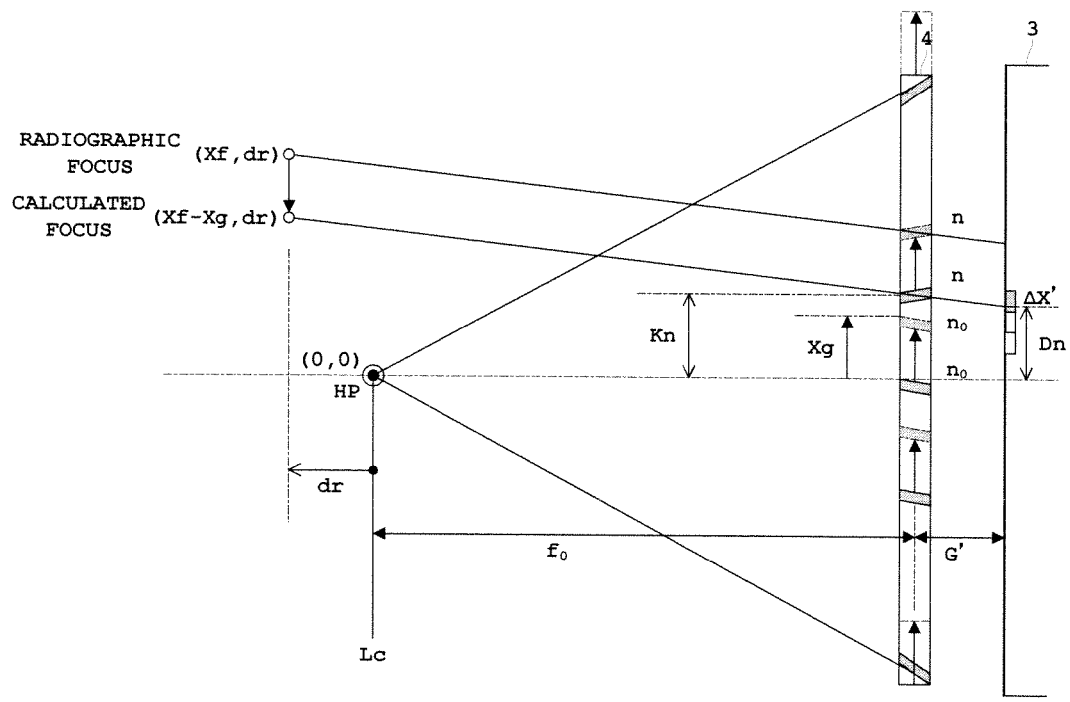
FIG. 6 is a schematic view when the bending constant is applied to actual radiography.
Figure 7:
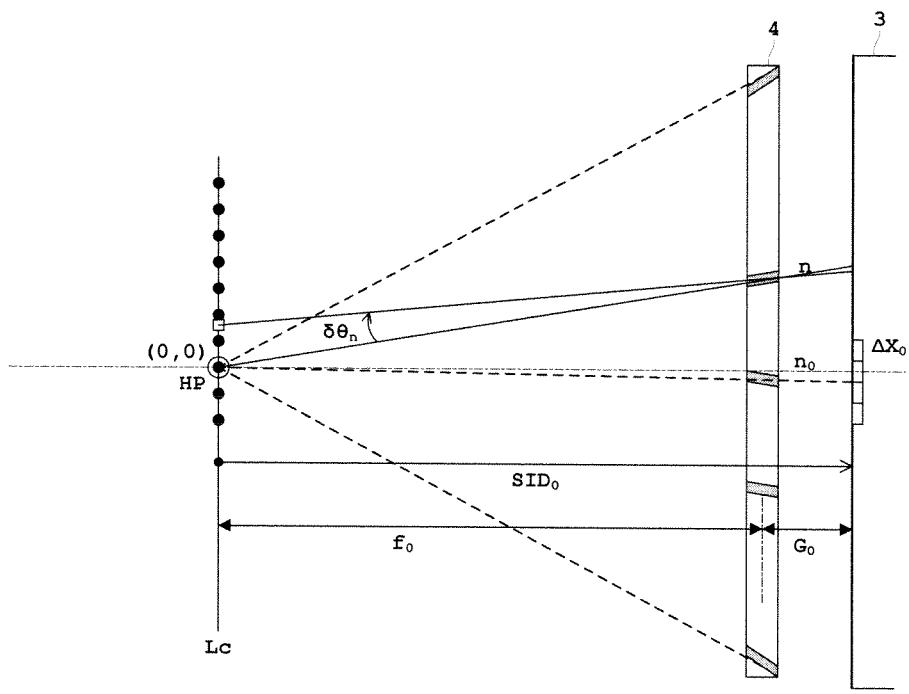
FIG. 7 is a schematic view showing a positional relationship when obtaining a twisting constant.
Figure 8:
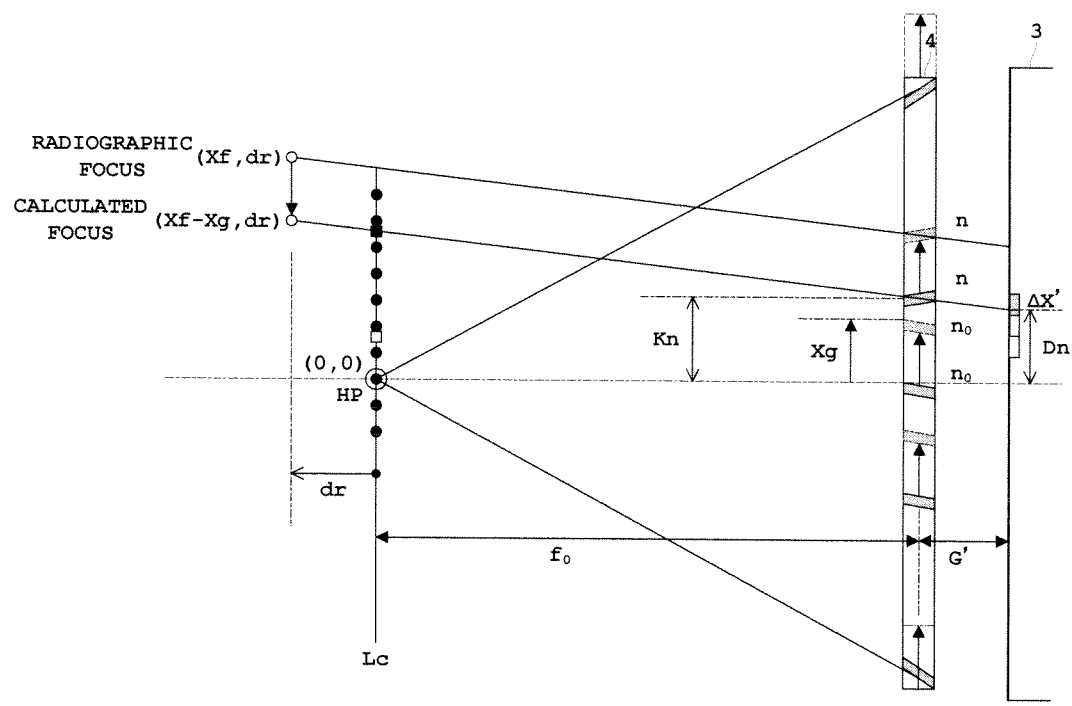
FIG. 8 is a schematic view when the twisting constant is applied to actual radiography.
Figure 9:
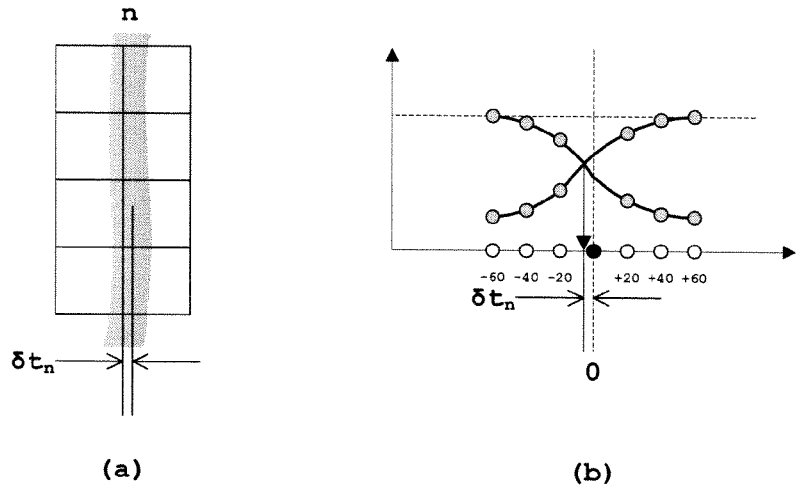
FIG. 9 is a schematic view schematically showing calculation of the bending constant.
Figure 10:
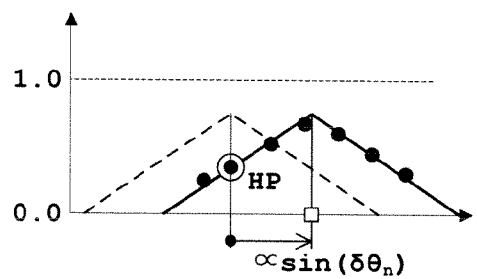
FIG. 10 is a schematic view of a profile of a straddle accumulated value of reference correction data.
Figure 11:
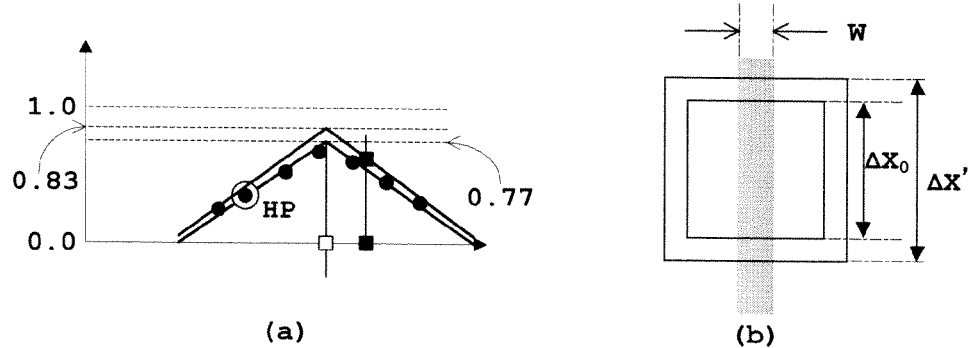
FIG. 11 is a schematic view illustrating multiplication of the straddle accumulated value of reference correction data by a predetermined multiplying factor.

Next, the image processor and a flow of a series of image processes will be described with reference to FIGS. 4-11. FIG. 4 is a block diagram of a specific image processor according to the embodiment. FIG. 5 is a schematic view showing a positional relationship when obtaining a bending constant. FIG. 6 is a schematic view when the bending constant is applied to actual radiography. FIG. 7 is a schematic view showing a positional relationship when obtaining a twisting constant. FIG. 8 is a schematic view when the twisting constant is applied to actual radiography. FIG. 9 is a schematic view schematically showing calculation of the bending constant. FIG. 10 is a schematic view of a profile of a straddle accumulated value of reference correction data. FIG. 11 is a schematic view illustrating multiplication of the straddle accumulated value of reference correction data by a predetermined multiplying factor.

The image processor 11, as shown in FIG. 4, includes a correction data collecting unit 31, a radiological image collecting unit 32, a first accumulated value calculating unit 33, an accumulated value multiplying unit 34, a corresponding corrected image calculating unit 35, a foil shadow aligned image generating unit 36, a lowpass filter (hereinafter abbreviated as "LPF") 37, a second accumulated value calculating unit 38, a false image removing foil shadow image generating unit 39 and a false image removed image generating unit 40. The correction data collecting unit 31 has a bending constant calculating unit 31a and a twisting constant calculating unit 31b. The bending constant calculating unit 31a corresponds to the bending constant calculating device in this invention. The twisting constant calculating unit 31b corresponds to the twisting constant calculating device in this invention. The radiological image collecting unit 32 corresponds to the radiological image collecting device in this invention. The first accumulated value calculating unit 33 and second accumulated value calculating unit 38 correspond to the accumulated value calculating device in this invention. The accumulated value multiplying unit 34 corresponds to the accumulated value multiplying device in this invention.

Here, a home position (HP: Home Position) is a converging position of foil inclinations in an ideal case where the grid foil strips 4a are free from bending and twisting, which refers to a focal position HP located on a center line of the FPD 3 and X-ray grid 4 as shown in FIGS. 5-8 and located at a distance of $f_0$ from the X-ray grid 4. SID is, when a perpendicular is drawn from the focal position on the X-ray tube 2 to the FPD 3, a distance from the focal position in the perpendicular direction to the FPD 3 (SID: Source Image Distance), and $f_0$ is a distance (focusing distance) between the home position HP and a center plane of the X-ray grid 4.

As shown in FIGS. 5-8, the coordinates of the home position HP are set to (0, 0). When, as shown in FIGS. 6 and 8, a transverse focal shift amount of the X-ray tube 2 (see FIG. 1) (focal shift amount along the installation plane direction of the FPD 3 and X-ray grid 4 from the home position HP) is Xf and a longitudinal focal shift amount (focal shift amount along the perpendicular direction from the home position HP) is dr, the coordinates of an actual radiographic focus will become (Xf, dr). When it is assumed that a grid foil strip 4a serving as reference is located on the center line of the FPD 3 and X-ray grid 4, and that this grid foil strip 4a has shifted as a result of grid attachment and detachment, for example, the shift amount is set to Xg.

Since the longitudinal shift amount dr is set as a use situation of the X-ray apparatus, it is an amount readable from the apparatus and is known. The following description will be made on the assumption that the transverse focal shift amount Xf and grid shift amount Xg at the time of actual radiography are also known from a marker process, a correlation process by foil shadows, or other processes.

The correction data collecting unit 31 collects reference correction data before shipment. In particular, the bending constant calculating unit 31a calculates a bending constant, and a twisting constant calculating unit 31b calculates reference correction data having twisting constant information.

The radiological image collecting unit 32, when an actual radiological image is labeled I as shown in FIG. 4, collects the actual radiological image based on X-ray detection signals detected in the presence of the inspection object M (see FIG. 1). At the time of actual radiography, as shown in FIGS. 6 and 8, each pixel size is ΔX' and the distance between the detecting plane of the FPD 3 and the center plane of the X-ray grid 4 is G'. When collecting the reference correction data in advance of X-raying (eg before shipment of the X-ray grid 4), as shown in FIGS. 5 and 7, with each pixel size being $ΔX_0$ and the distance between the detecting plane of the FPD 3 and the center plane of the X-ray grid 4 being $G_0$, it is not absolutely necessary that $ΔX_0=ΔX'$ and $G_0=G'$. Even $ΔX_0≠ΔX'$ and $G_0≠G'$ will do. In other words, as noted in the Technical Problem section hereof, the following image processing is applicable in a way to accommodate radiation grids and radiation detecting devices of various sizes. The actual radiological image I collected by the radiological image collecting unit 32 is fed to the foil shadow aligned image generating unit 36.

The bending constant calculating unit 31a, when the bending constant is labeled $δt_n$ as shown in FIG. 4, calculates bending constant $δt_n$ which is a constant relating to bending of the grid foil strips 4a in locations where the foil shadows cast from the grid foil strips 4a straddle pixels. Specifically, a correction data collecting device having a layout as shown in FIG. 5 is used to move the X-ray grid 4 at predetermined intervals (eg about 20 μm) along the installation plane of the X-ray grid 4 in the absence of an inspection object, and bending constant $δt_n$ is obtained by collecting signal strengths of the straddle position pixels. When obtaining reference correction data having twisting constant $\delta\theta_n$ information, a correction data collecting device having a layout as shown in FIG. 7 is used.

When collecting the reference correction data, in the absence of an inspection object, the focus is moved from the home position HP at predetermined intervals (eg about 1 mm) along a focus line Lc as shown in FIG. 7, and an X-ray image is collected for every focal position as reference correction data through the FPD 3. At this time, the reference correction data is collected using a device other than the X-ray apparatus used for actual radiography, which is a correction data collecting device which does not easily produce shifting of the positional relationship. Of course, when an X-ray apparatus of the type which does not easily produce focal shifting from one radiography to another, the same X-ray apparatus may be used to collect the reference correction data.

Returning to the description of FIG. 5, in the state of the focus of the X-ray tube 2 (see FIG. 1) set to the home position HP, X-ray detection signals are collected, respectively, by moving the X-ray grid 4 at predetermined intervals along the installation plane of the X-ray grid 4 as described above. The grid foil strip 4a used as reference is an $n_0$th foil strip which is the $n_0$th in order, and a target grid foil strip 4a is an nth foil strip which is the nth in order. At this time, each signal strength of the X-ray detection signals in a plurality of pixels straddling the foil shadow by the nth target foil strip is collected as signal strength of a straddle position pixel. Although the $n_0$th foil strip serving as the reference is the grid foil strip 4a located on the center line in FIGS. 5-8, this is not limitative and, for example, a grid foil strip 4a located at an end may be used as the foil strip serving as the reference.

To describe that a foil shadow straddles two pixels in the case of FIG. 5, signal strengths of the two pixels straddling the foil shadow by the nth foil strip serving as the target are collected, respectively, as signal strengths of the straddle position pixels as shown in FIG. 9(b). In FIG. 9(b), the horizontal axis represents amount of movement of the X-ray grid 4, and the vertical axis represents signal strength.

When there is no bending of the grid foil strips 4a, and assuming that the boundary between the two pixels straddles the center of the foil shadow, the position where the signal strengths of the straddle position pixels intersect each other should be located at the boundary between the two pixels. In practice, however, due to bending of the grid foil strips 4a, as shown in FIG. 9(b), the signal strengths of the straddle position pixels intersect each other in a position deviating from the boundary (shown in a dotted line) between the two pixels. This deviation of the intersecting position from the boundary between the two pixels is defined as bending constant (see also FIG. 9(a)) $\delta t_n$. FIG. 9(a) is a schematic view of the foil shadow by the nth foil strip projected in a bent state on the pixels. This bending constant $\delta t_n$ is obtained for each pixel row and each grid foil strip 4a. The bending constant described here and also the twisting constant described hereinafter, of course, differ from foil strip to foil strip, and vary also for each position in the foil running direction (row), but this embodiment is described as treatment in a fixed row position.

In this way, the bending constant calculating unit 31a calculates bending constant $\delta t_n$ as shown in FIG. 4. The bending constant $\delta t_n$ calculated by the bending constant calculating unit 31a is fed to the first accumulated value calculating unit 33 and second accumulated value calculating unit 38.

When applying bending constant $\delta t_n$ to actual radiography, foil shadow pixels at the time of actual radiography are identified by calculating Kn and also calculating Dn as shown in FIG. 6. In FIGS. 6 and 8, the X-ray grid 4 shifted at the time of actual radiography (grid arrangement at the time of radiography) is indicated in two-dot chain lines, to show it in distinction from the X-ray grid 4 at the time of calculation (grid arrangement at the time of calculation) which is indicated in solid lines. When the focus shifted by grid shift amount Xg from the actual radiographic focus (Xf, dr) is a calculated focus, the coordinates of the calculated focus are (Xf−Xg, dr) as shown in FIGS. 6 and 8.

When the distance between the nth target foil strip in the grid arrangement at the time of calculation and the center line (of the FPD 3 and X-ray grid 4) is Kn, distance Ku (that is, position from the center line of the nth foil strip) can be derived from the following equation (1):

$$Kn=(n-n_0)\cdot P+\delta t_n \quad (1)$$

where P is an ideal foil strip pitch, and P is known. Bending constant $\delta t_n$ also has already been obtained. Therefore, distance Kn can be obtained since the right-hand side of equation (1) above is known.

When, among the rays from the calculated focus (Xf−Xg, dr), the distance of a position projected on the FPD 3 through the nth foil strip in the grid arrangement at the time of calculation and the center line is Dn, distance Dn can be obtained based on the geometric positional relationship of the following equation (2):

$$Dn=Kn-\{(Xf-Xg-Kn)\cdot G'/(f_0+dr)\} \quad (2)$$

As described hereinbefore, $f_0$ is the distance (focusing distance) between the home position HP and the center plane of the X-ray grid 4, and $f_0$ is known. It is premised that the longitudinal focal shift amount dr, and the distance G' between the detecting plane of the FPD 3 and the center plane of the X-ray grid 4, are known, and that each of the shift amounts Xf and Xg is known as noted above. The distance Kn which is the position from the center line of the nth foil strip has already been derived from equation (1) above. Therefore, distance Dn can be obtained since the right-hand side of equation (2) above is known.

Next, foil shadow pixels are identified as locations where the foil shadows of the grid foil strips 4a straddle pixels, using the distance Dn derived from equation (2) above and pixel size $\Delta X'$ at the time of actual radiography. Specifically, the distance Dn is divided by pixel size $\Delta X'$, and foil shadow pixels are identified from the integer portion of the division result $Dn/\Delta X'$, and detailed straddle positions from the fractional portion thereof. A straddle accumulated value of the nth foil strip at the time of radiography is obtained by subtracting the signal strengths of the identified foil shadow pixels from the signal strengths at the time when it is assumed that there is no foil shadow. By obtaining this for each pixel row and each grid foil strip 4a, the first accumulated value calculating unit 33 can calculate a straddle accumulated value of reference correction data described hereinafter, and the second accumulated value calculating unit 38 can calculate a straddle accumulated value of a foil shadow enhanced image based on an actual radiological image described hereinafter.

The first accumulated value calculating unit 33, as shown in FIG. 4, in a location where foil shadows of the grid foil strips 4a straddle pixels, identifies this location based on a mutual geometric positional relationship (that is, geometry) of the X-ray tube 2, FPD 3 and X-ray grid 4 (see FIG. 1 for all), and calculates a straddle accumulated value of the foil shadows in the identified location. Similarly, the second accumulated value calculating unit 38 identifies the location based on geometry, and calculates a straddle accumulated value of the foil shadows in the identified location. There are two straddle accumulated values, which are a straddle accumulated value of the reference correction data described hereinafter and a straddle accumulated value of a foil shadow enhanced image based on an actual radiological image described hereinafter. As noted above, the first accumulated value calculating unit 33 calculates the straddle accumulated value of the reference correction data, and the second accumulated value calculating unit 38 calculates the straddle accumulated value of the foil shadow enhanced image.

As noted hereinbefore, twisting or bending of each grid foil strip 4a does not necessarily cause its foil shadow to straddle or cover the pixels. Depending on a twist or bend situation, the foil shadow may not cover even one pixel but may cover other pixels (eg adjacent pixels). In that case, pixels in a location considered likely to be straddled by the foil shadow are recognized from the mutual geometric positional relationship (that is, geometry) of the X-ray tube 2, FPD 3 and X-ray grid 4, and straddle accumulated values in that location are calculated uniformly, regardless of a foil shadow straddle situation.

The straddle accumulated value of the reference correction data based on calculation by the first accumulated value calculating unit 33 will be described in detail. A profile of the straddle accumulated value of the reference correction data is obtained as shown in FIG. 10. In FIG. 10, the horizontal axis represents amounts of focal movement, and the vertical axis represents ratios between the denominator which is a signal strength when assuming that there is no foil shadow, and the numerator which is a straddle accumulated value of the nth foil strip, thereby creating a profile of the straddle accumulated value of the nth foil strip.

When there is no twist in the grid foil strips 4a, the profile is as shown in the dotted lines in FIG. 10. In practice, however, due to twisting occurring to the grid foil strips 4a, the profile becomes what is shown in the solid lines in FIG. 10. Then, the twisting constant calculating unit 31b calculates a twisting constant.

The twisting constant calculating unit 31b, when the twisting constant is labeled $\delta\theta_n$ as shown in FIG. 4, calculates twisting constant $\delta\theta_n$ which is a constant relating to twisting of the grid foil strips 4a. When calculating twisting constant $\delta\theta_n$ as above, the correction data collecting device shown in FIG. 7 is used, which is the same as what is shown in FIG. 5.

When, as shown in FIG. 7, there is a twist at twist angle $\delta\theta_n$ from an ideal angle of the nth foil strip, a ray forming twist angle $\delta\theta_n$ with a ray passing through the nth foil strip serving as the target is defined from among the rays from the home position HP. A profile of the straddle accumulated value based on the data at the focus (indicated by a void square: "□" in FIG. 7) at which this defined ray and the focus line Lc meet becomes a profile as shown in the solid lines in FIG. 10. Therefore, a shifting in an amount of focal movement from the profile of the nth ideal foil strip as shown in the dotted lines in FIG. 10 can be detected by collecting data in the state of the grid foil strip 4a being twisted, and creating the profile (solid lines in FIG. 10) based thereon. Since the shifting at this time is an amount (indicated "$\propto \sin(\delta\theta_n)$" in FIG. 10) proportional to $\sin(\delta\theta_n)$, it is possible to obtain twisting constant $\delta\theta_n$ directly, but a straddle accumulated value for each $\sin(\delta\theta_n)$ is stored in order to reduce the amount of calculation. This is called reference correction data having twisting constant $\delta\theta_n$ information. Each mark in FIG. 7, each mark in FIG. 8 and each mark in FIG. 10 are unified (for example, focus □ where the ray and the focus line Lc meet is common to FIGS. 7, 8 and 10).

In this way, the twisting constant calculating unit 31b calculates twisting constant $\delta\theta_n$ (reference correction data) as shown in FIG. 4. The twisting constant $\delta\theta_n$ (reference correction data) calculated by the twisting constant calculating unit 31b is fed to the first accumulated value calculating unit 33.

When applying twisting constant $\delta\theta_n$ (reference correction data) to actual radiography, as shown in FIG. 8, Kn is calculated, and further Dn is calculated, thereby to determine a point of intersection with the focus line Lc (indicated by a black square: "■" in FIG. 8). Since this intersection is not necessarily in agreement with the focal position of the time when the reference correction data is collected, an nth straddle accumulated value of a corresponding corrected image is obtained, for example, by making linear interpolation through weighting correction from straddle accumulated values in two adjacent focal positions. Therefore, when located at midpoint between focal positions, linear interpolation may be carried out with the same weighting of straddle accumulated values in two adjacent focal positions. The method of calculating Kn and Dn has been described in FIG. 6, and its description is omitted here. When the intersection (■ in FIG. 8) with the focus line Lc is located in the peak position of the profile, extrapolation may be carried out from opposite sides.

Thus, the first accumulated value calculating unit 33 calculates a straddle accumulated value of the reference correction data, using the bending constant $\delta t_n$ calculated by the bending constant calculating unit 31a and the twisting constant $\delta\theta_n$ calculated by the twisting constant calculating unit 31b (reference correction data). As described above, the straddle accumulated value of the nth foil strip of the reference correction data is obtained by subtracting the signal strengths in the identified foil shadow pixels in the reference correction data from the signal strengths in the reference correction data of the time when assuming that there is no foil shadow. Since calculation is carried out for the foil position reflecting bending constant $\delta t_n$ at this time, the straddle accumulated value of the reference correction data can be calculated accurately.

In this way, the first accumulated value calculating unit 33 calculates the straddle accumulated value of the reference correction data as shown in FIG. 4. The straddle accumulated value of the reference correction data calculated by the first accumulated value calculating unit 33 is fed to the accumulated value multiplying unit 34 and corresponding corrected image calculating unit 35.

The accumulated value multiplying unit 34, as shown in FIG. 4, multiplies the straddle accumulated value of the reference correction data by a predetermined multiplying factor based on the width and pixel size of the foil shadow. As described hereinbefore, pixel size $\Delta X_0$ at the time of collecting the reference correction data and pixel size $\Delta X'$ at the time of actual radiography are not necessarily equal. In FIG. 11, the width of the foil shadow is fixed to W (see FIG. 11(b)) for simplification. Assuming that $\Delta X_0=150$ μm (=0.15 mm), $\Delta X'=200$ μm (=0.2 mm) and W=0.034 mm, the peak value of the profile of the straddle accumulated values, as shown in FIG. 11(a), is 0.77 ($\Delta X_0-W)/\Delta X_0=(0.2-0.034)/0.2$) at the time of collecting the reference correction data, and is 0.83 (=$(\Delta X'-W)/\Delta X'=(0.15-0.034)/0.15$) at the time of actual radiography. Each mark in FIG. 7, each mark in FIG. 8, each mark in FIG. 10 and each mark in FIG. 11(*a*) are unified (for example, focus □ where the ray and the focus line Lc meet is common to FIGS. 7, 8, 10 and 11(*a*), and intersection ■ with the focus line Lc is common to FIGS. 8 and 11(*a*)).

In this way, the accumulated value multiplying unit 34, as shown in FIG. 4, multiplies the straddle accumulated value of the reference correction data by the multiplying factor (0.83/0.77 here). The straddle accumulated value of the reference correction data multiplied by the accumulated value multiplying unit 34 is fed to the corresponding corrected image calculating unit 35.

Based on the straddle accumulated value of the reference correction data multiplied by the accumulated value multiplying unit 34, the corresponding corrected image calculating unit 35 determines a ray from the calculated focus shifted from an actual radiographic locus by the grid shift amount Xg (see FIGS. 6 and 8), and obtains a corresponding corrected image corresponding to that ray.

As described also in FIGS. 6 and 8, the coordinates of the calculated focus shifted from the actual radiographic focus (Xf, dr) by the grid shift amount Xg are (Xf−Xg, dr). At this time, if reference correction data at the intersection (indicated by black square: "■" in FIG. 8) of the ray passing through the nth foil strip, among the rays from the calculated focus (Xf−Xg, dr), and the focus line Lc (see FIGS. 6 and 8), a corresponding corrected image of that time can be obtained. When the intersection at which the ray concerned and the focus line Lc meet is in agreement with the focal position of the time when the reference correction data is collected, the reference correction data (X-ray image) in that focal position may serve as it is as the corresponding corrected image.

However, the intersection at which the ray concerned and the focus line Lc meet is not necessarily in agreement with the focal position of the time when the reference correction data is collected. In that case, a corresponding corrected image can be obtained by making weighting correction using reference correction data (X-ray images) in two focal positions closest to the intersection (that is, adjoining each other) at which the ray concerned and the focus line Lc meet, respectively. A corresponding corrected image can be obtained, for example, by allotting to each pixel a pixel value (value of X-ray detection signal) which is a sum of a product of reference correction data in one of the adjacent focal positions and a weighting function of that time, and a product of reference correction data in the other focal position and the weighting function of that time.

In this way, the corresponding corrected image calculating unit 35 calculates a corresponding corrected image as shown in FIG. 4. Since the straddle accumulated value of the reference correction data is already obtained by the first accumulated value calculating unit 33, assuming that the accumulated value in the corresponding corrected image (the nth straddle accumulated value of the above corresponding corrected image) is $C_{sum}$, the accumulated value $C_{sum}$ in the corresponding corrected image is fed to the false image removing foil shadow image generating unit 39.

When a foil shadow aligned image is labeled G as shown in FIG. 4, the foil shadow aligned image generating unit 36 generates the foil shadow aligned image G, which is a radiological image showing aligned foil shadows, by sliding the radiological image I in the direction of arrangement of the grip foil strips 4*a* (lateral direction in FIG. 3). The foil shadow aligned image G can be generated by sliding the radiography image I with information on the inspection object, using the grid shift amount Xg described above.

When generating a foil shadow aligned image G with higher precision, a precise foil shadow aligned image G can be generated by obtaining a shift amount (grid shift amount Xg) for each pixel row and sliding the radiological image I for each pixel row. There remains a shift amount in the extending direction of the grid foil strips 4*a* (vertical direction in FIG. 3), but such shift amount is slight and thus negligible.

In this way, the foil shadow aligned image generating unit 36 generates the foil shadow aligned image G as shown in FIG. 4. The foil shadow aligned image G generated by the foil shadow aligned image generating unit 36 is fed to the LPF 37 and false image removed image generating unit 40.

The LPF 37, when the foil shadow enhanced image is labeled E as shown in FIG. 4, passes low-pass areas in the longitudinal direction of the grid foil strips 4*a* (vertical direction in FIG. 3) in order to generate the foil shadow enhanced image E enhancing the foil shadows in the foil shadow aligned image G and with the information on the inspection object M (see FIG. 1) removed therefrom. The foil shadow enhanced image F generated by the LPF 37 is fed to the second accumulated value calculating unit 38.

The second accumulated value calculating unit 38, when a straddle accumulated value of the foil shadow enhanced image E is labeled $E_{sum}$ as shown in FIG. 4, calculates the accumulated value $E_{sum}$. The accumulated value $E_{sum}$ is fed to the false image removing foil shadow image generating unit 39.

The false image removing foil shadow image generating unit 39, when a false image removing foil shadow image is labeled Cor as shown in FIG. 4, can generate the false image removing foil shadow image Cor for removing false images resulting from the foil shadows based on the accumulated values $E_{sum}$ and sum ($Cor = E \cdot C_{sum}/E_{sum}$).

In this way, the false image removing foil shadow image generating unit 39 generates the false image removing foil shadow image Cor as shown in FIG. 4. The false image removing foil shadow image Cor generated by the false image removing foil shadow image generating unit 39 is fed to the false image removed image generating unit 40.

The false image removed image generating unit 40, when an X-ray image finally obtained by having the foil shadows removed is labeled $I_{after}$ as shown in FIG. 4, generates the false image removed image without the foil shadows by the grid foil strips 4*a*, based on the false image removing foil shadow image Cor. And the false image removed image generated by the false image removed image generating unit 40 is finally obtained as X-ray image $I_{after}$. The X-ray image $I_{after}$ can be obtained by dividing the foil shadow aligned image G by the false image removing foil shadow image Cor for each pixel ($I_{after} = G/Cor$).

Since the interspacers are voids in the case of an air grid, the contrast between pixels straddled by the foil shadows and pixels not straddled is strong, and the false images are conspicuous. The problem addressed by the invention is solvable by applying the image processor and the flow of a series of image processes described above to the air grid.

The X-ray apparatus according to this embodiment includes, besides the X-ray tube 2, FPD 3 and X-ray grid 4, the first accumulated value calculating unit 33 and second accumulated value calculating unit 38 which, in a location where the foil shadows by the grid foil strips 4*a* straddle pixels, identify this location based on a mutual geometric positional relationship of the X-ray tube 2, FPD 3 and X-ray grid 4, and calculate straddle accumulated values of the foil shadows in the identified location. And the radiological image collecting unit 32 is provided for collecting an actual radiological image based on X-ray detection signals detected in the presence of an inspection object M. An X-ray image is finally obtained by removing the foil shadows by the grid foil strips 4a based on the above first and second accumulated value calculating units 33 and 38 and the above radiological image collecting unit 32. Even when the foil shadows by the grid foil strips 4a straddle the pixels due to twisting and bending of the grid foil strips 4a, such location is identified based on the mutual geometric positional relationship (that is, geometry) of the X-ray tube 2, FPD 3 and X-ray grid 4, and the straddle accumulated values of the foil shadows in the identified location are calculated. Therefore, even when changes are made in the sizes of the X-ray grid 4 and FPD 3, the foil shadows will be removed based on the straddle accumulated values. As a result, the foil shadows can be removed taking twisting and bending of the grid foil strips 4a into consideration, and in a way to accommodate X-ray grids 4 and FPDs 3 of various sizes.

In this embodiment, it is preferred to provide the bending constant calculating unit 31a for calculating a bending constant which is a constant relating to bending of the grid foil strips 4a in the location where the foil shadows by the grid foil strips 4a straddle the pixels, wherein the X-ray image is finally obtained by removing the foil shadows by the grid foil strips 4a based on the first and second accumulated value calculating units 33 and 38, the bending constant calculating unit 31a and the radiological image collecting unit 32. By removing the foil shadows by the grid foil strips 4a using also the bending constant which is a numerical expression of bending, the foil shadows can be removed with increased precision through greater consideration made of the bending of the grid foil strips 4a.

In this embodiment, it is preferred to provide the twisting constant calculating unit 31b for calculating a twisting constant which is a constant relating to twisting of the grid foil strips 4a, wherein the X-ray image is finally obtained by removing the foil shadows by the grid foil strips 4a based on the first and second accumulated value calculating units 33 and 38, the twisting constant calculating unit 31b and the radiological image collecting unit 32. By removing the foil shadows by the grid foil strips 4a using also the twisting constant which is a numerical expression of twisting, the foil shadows can be removed with increased precision through greater consideration made of the twisting of the grid foil strips 4a.

In this embodiment, it is preferred to provide the accumulated value multiplying unit 34 for multiplying a straddle accumulated value of reference correction data based on X-ray detection signals detected in the absence of the inspection object by a predetermined multiplying factor based on the width and pixel size of the foil shadows. By multiplying the straddle accumulated value of the reference correction data by the predetermined multiplying factor, the X-ray image without the foil shadows can be obtained in a way to accommodate the X-ray grids 4 and FPD 3 of various sizes. It is therefore possible to perform an appropriate false image removing process using one X-ray grid, without manufacturing an X-ray grid according to each FPD or geometry.

This invention is not limited to the foregoing embodiment, but may be modified as follows:

(1) The foregoing embodiment has been described taking X-rays as an example of radiation. However, the invention is applicable to radiation other than X-rays (such as gamma rays).

(2) In the foregoing embodiment, the X-ray apparatus is an apparatus having a C-arm for application to CVS systems, but this is not limitative. For example, the apparatus may be constructed like a nondestructive testing apparatus for industrial use which conducts radiography of an object (in this case, a subject tested) conveyed on a belt, or may be constructed like an X-ray CT apparatus for medical use.

(3) In the foregoing embodiment, an air grid is employed as radiation grid, but this is not limitative. The grid may have, in place of the voids, an intermediate material such as aluminum or organic substance which transmits radiation represented by X-rays. Further, the grid may be a cross grid. In the case of a cross grid, grid shifting is less likely to occur than the air grid with grid foil strips extending only in one direction, but of course, it is applicable. In this case, the direction of shifting may be determined with an extension from one direction to two directions.

(4) The foregoing embodiment provides a focused grid, but the invention is applicable also to a grid of parallel arrangement.

(5) The foregoing embodiment has been described in relation to a grid synchronous (synchronous grid) with the pixels (see $\Delta X_0$ in FIGS. 5 and 7) of the FPD 3 at the time of correction data collection, but the invention may be applied to an asynchronous grid. In the case of a grid other than the air grid, it may be applied to a grid having a construction in which a plurality of grid foil strips are juxtaposed for one pixel.

(6) The foregoing embodiment provides the bending constant calculating device (bending constant calculating unit 31a in the embodiment) and the twisting constant calculating device (twisting constant calculating unit 31b in the embodiment) in order to calculate a bending constant and a twisting constant which are numerical expressions of bending and twisting, respectively. If there is little influence of bending and twisting, only the accumulated value calculating devices (first and second accumulated value calculating units 33 and 38) may be provided for calculating straddle accumulated values based on geometry.

(7) In the foregoing embodiment, the straddle accumulated value of reference correction data is multiplied by the predetermined multiplying factor based on the width and pixel size of the foil shadows. However, where the X-ray grid 4 and FPD 3 are the same size, or geometry is the same, it is not absolutely necessary to multiply the straddle accumulated value of reference correction data by the predetermined multiplying factor.

(8) In the foregoing embodiment, the straddle accumulated values are data relating to the reference correction data and the foil shadow enhanced image, but this is not (imitative. For example, straddle accumulated values relating to the radiological image may be obtained.

REFERENCE SIGNS LIST

2 . . . X-ray tube
3 . . . flat panel X-ray detector (FPD)
4 . . . X-ray grid
4a . . . grid foil strips
31a . . . bending constant calculating unit
31b . . . twisting constant calculating unit
32 . . . radiological image collecting unit
33 . . . first accumulated value calculating unit
34 . . . accumulated value multiplying unit
38 . . . second accumulated value calculating unit
M . . . inspection object

The invention claimed is:

1. A radiographic apparatus for obtaining a radiological image, comprising:
   a radiation source for emitting radiation;
   a radiation detector for detecting the radiation from the radiation source;
   a radiation grid disposed adjacent to a detecting plane of the radiation detector, and having an arrangement of grid foil strips for absorbing scattered radiation; and
   a processor configured to:
      in a location where foil shadows by the arrangement of grid foil strips straddle pixels, identify the location based on a mutual geometric positional relationship of the radiation source, the radiation detector and the radiation grid, and calculate a straddle accumulated value of the foil shadows in the identified location, the pixels corresponding respectively to positions of detecting elements in the radiation detector;
      obtain an actual radiological image based on radiation detection signals from the radiation detector, the radiation detection signals being obtained in the presence of an inspection object between the radiation source and the radiation detector;
      calculate a bending constant which is a constant relating to bending of the arrangement of grid foil strips in the location where the foil shadows by the arrangement of grid foil strips straddle the pixels; and
      remove from the actual radiological image the foil shadows by the arrangement of grid foil strips based on the straddle accumulated value and the bending constant.

2. The radiographic apparatus according to claim 1, wherein the processor is further configured to:
   calculate a twisting constant which is a constant relating to twisting of the arrangement of grid foil strips; and
   remove from the corrected actual radiological image the foil shadows by the arrangement of grid foil strips based on the straddle accumulated value, the bending constant, and the twisting constant.

3. The radiographic apparatus according to claim 1, wherein the processor is further configured to multiply the straddle accumulated value of reference correction data based on X-ray detection signals detected in the absence of the inspection object by a predetermined multiplying factor based on width and pixel size of the foil shadows.

4. A radiographic apparatus for obtaining a radiological image, comprising:
   a radiation source for emitting radiation;
   a radiation detector for detecting the radiation from the radiation source emitted;
   a radiation grid disposed adjacent to a detecting plane of the radiation detector, and having an arrangement of grid foil strips for absorbing scattered radiation;
   a processor configured to:
      in a location where foil shadows by the arrangement of grid foil strips straddle pixels, identify the location based on a mutual geometric positional relationship of the radiation source, the radiation detector and the radiation grid, and calculate a straddle accumulated value of the foil shadows in the identified location, the pixels corresponding respectively to positions of detecting elements in the radiation detector;
      obtain an actual radiological image based on radiation detection signals from the radiation detector, the radiation detection signals being obtained in the presence of an inspection object between the radiation source and the radiation detector; and
      calculate a twisting constant which is a constant relating to twisting of the arrangement of grid foil strips in the location where the foil shadows by the arrangement of grid foil strips straddle the pixels,
      remove from the actual radiological image the foil shadows by the arrangement of grid foil strips based on the straddle accumulated value and the twisting constant.

5. The radiographic apparatus according to claim 4, wherein the processor is further configured to multiply the straddle accumulated value of reference correction data based on X-ray detection signals detected in the absence of the inspection object by a predetermined multiplying factor based on width and pixel size of the foil shadows.

* * * * *